(12) United States Patent
Aiken

(10) Patent No.: US 8,114,060 B2
(45) Date of Patent: Feb. 14, 2012

(54) CONTAINMENT DEVICE WITH INDICATOR

(75) Inventor: Brian Aiken, East Aurora, NY (US)

(73) Assignee: Mattel, Inc., El Segundo, CA (US)

( * ) Notice: Subject to any disclaimer, the term of this patent is extended or adjusted under 35 U.S.C. 154(b) by 288 days.

(21) Appl. No.: 12/412,500

(22) Filed: Mar. 27, 2009

(65) Prior Publication Data

US 2009/0247980 A1    Oct. 1, 2009

Related U.S. Application Data

(60) Provisional application No. 61/099,159, filed on Sep. 22, 2008, provisional application No. 61/041,270, filed on Apr. 1, 2008.

(51) Int. Cl.
*A61F 13/15* (2006.01)
(52) U.S. Cl. ......... 604/389; 604/387; 604/391; 604/396
(58) Field of Classification Search ............. 604/387, 604/389, 391, 394, 396
See application file for complete search history.

(56) References Cited

U.S. PATENT DOCUMENTS

| | | | |
|---|---|---|---|
| 3,613,679 A | 10/1971 | Bijou | |
| 3,848,594 A | 11/1974 | Buell | |
| 4,662,875 A | 5/1987 | Hirotsu et al. | |
| 5,195,950 A | 3/1993 | Delannoy | |
| 5,779,659 A | 7/1998 | Allen | |
| 6,050,967 A | 4/2000 | Walker et al. | |
| 6,142,968 A | 11/2000 | Pigg et al. | |
| 6,152,893 A | 11/2000 | Pigg et al. | |
| 6,329,564 B1 | 12/2001 | Lebner | |
| 6,338,723 B1 | 1/2002 | Carpenter et al. | |
| 6,432,074 B1 | 8/2002 | Ager et al. | |
| 6,689,116 B1 | 2/2004 | Ekdahl et al. | |
| 6,733,483 B2 | 5/2004 | Raufman et al. | |
| 6,822,133 B2 | 11/2004 | Lebner | |
| 6,831,205 B2 | 12/2004 | Lebner | |
| 7,347,845 B2 | 3/2008 | Zajaczkowski | |
| 2002/0062117 A1 | 5/2002 | Raufman et al. | |
| 2004/0073188 A1 | 4/2004 | Mitsui et al. | |
| 2004/0097896 A1 | 5/2004 | Raufman et al. | |
| 2004/0153046 A1 | 8/2004 | Ito et al. | |
| 2005/0033215 A1 | 2/2005 | Lebner | |
| 2005/0096618 A1 | 5/2005 | Magee et al. | |
| 2005/0217791 A1 | 10/2005 | Costello et al. | |
| 2006/0047259 A1 | 3/2006 | Erdman et al. | |
| 2006/0068168 A1 | 3/2006 | Olson et al. | |
| 2006/0212018 A1 | 9/2006 | Roe et al. | |
| 2006/0247594 A1 | 11/2006 | Nickel et al. | |
| 2007/0032773 A1 | 2/2007 | Magee et al. | |
| 2007/0049896 A1 | 3/2007 | Mills | |
| 2007/0066949 A1 | 3/2007 | Magee et al. | |
| 2007/0191752 A1 | 8/2007 | Lebner | |
| 2007/0250023 A1 | 10/2007 | Strannemalm | |

FOREIGN PATENT DOCUMENTS

WO    98/51247    11/1998

*Primary Examiner* — Jacqueline F. Stephens
(74) *Attorney, Agent, or Firm* — Edell, Shapiro & Finnan, LLC

(57) ABSTRACT

The present invention relates to a containment device. In particular, the present invention relates to a containment device with a closure mechanism that can be used to couple the containment device to a child. The closure mechanism may include or be used with one or more indicators that can be used by a parent or caregiver to determine whether the containment device is appropriately sized and tightened.

20 Claims, 10 Drawing Sheets

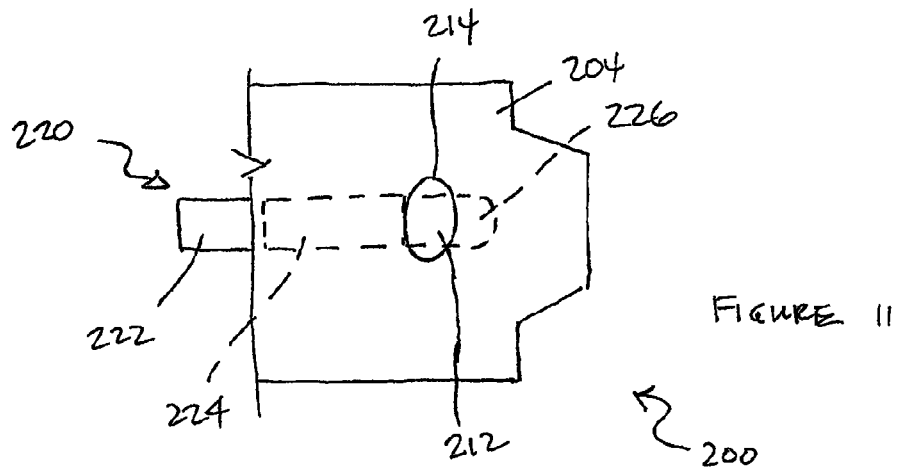
FIGURE 11
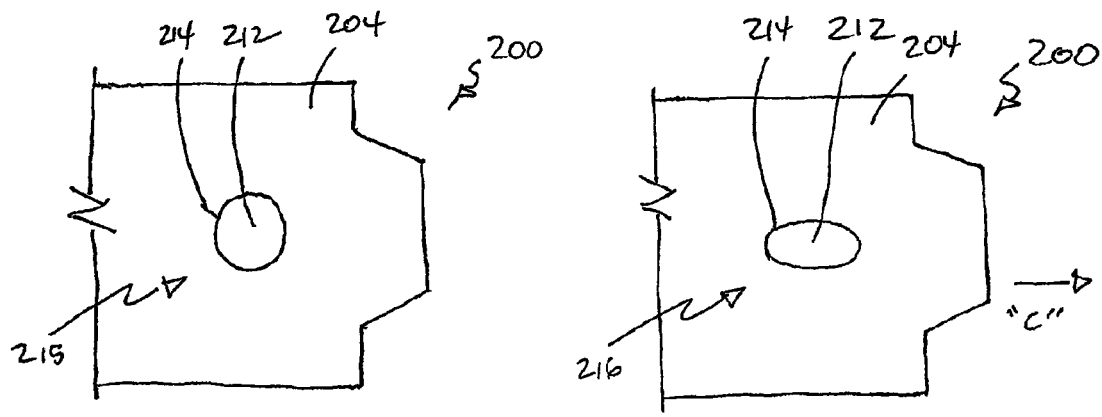
FIGURE 12
FIGURE 13
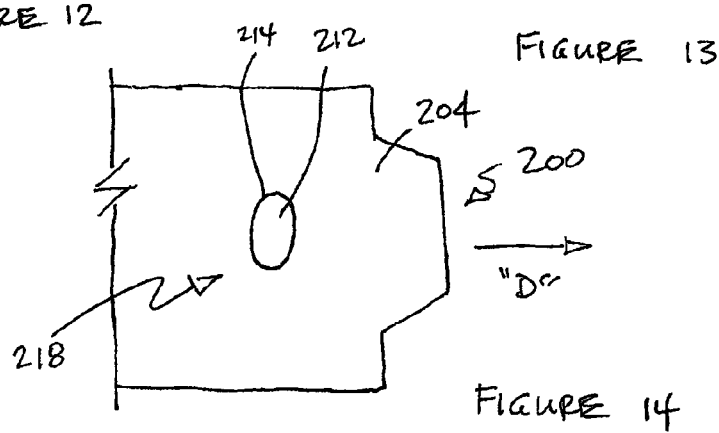
FIGURE 14

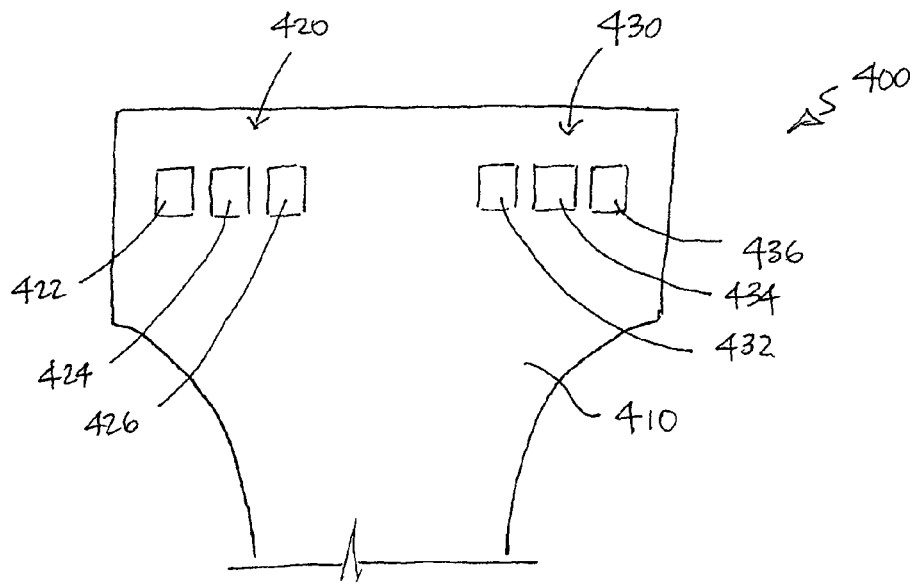
FIGURE 16
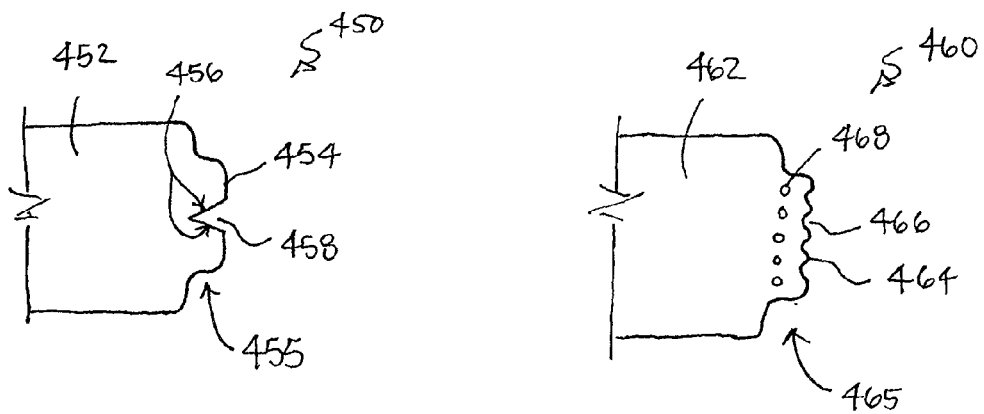
FIGURE 17
FIGURE 19
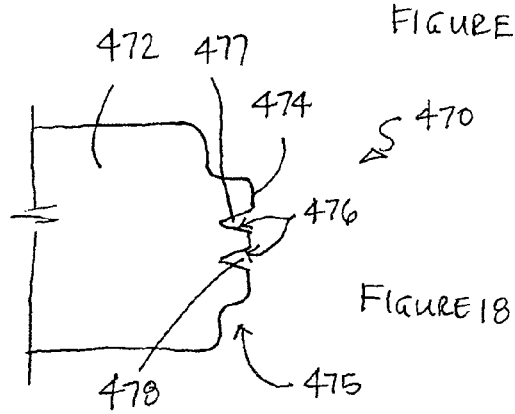
FIGURE 18

CONTAINMENT DEVICE WITH INDICATOR

REFERENCE TO RELATED APPLICATIONS

This application claims priority to and the benefit of U.S. Provisional Patent Application No. 61/041,270, entitled "Containment Device with Indicator," filed Apr. 1, 2008, the entire disclosure of which is incorporated herein by reference in its entirety. This application also claims priority to and the benefit of U.S. Provisional Patent Application No. 61/099,159, entitled "Containment Device with Indicator," filed Sep. 22, 2008, the entire disclosure of which is incorporated herein by reference in its entirety.

FIELD OF THE INVENTION

The present invention relates to a containment device. In particular, the present invention relates to a containment device with a closure mechanism that can be used to couple the containment device to a child. The closure mechanism may include or be used with one or more indicators that can be used by a parent or caregiver to determine whether the containment device is appropriately sized and tightened.

BACKGROUND OF THE INVENTION

There are many types of containment devices. One type of containment device is a diaper that can be worn by an infant or child. As infants or children grow, particular sizes of containment devices become too small. Sometimes containment devices are tightened too much, thereby making the infant or child uncomfortable. In addition, containment devices that are placed on an infant or child in a configuration that is too loose are not very helpful.

Therefore, a need exists for a containment device with an indicator or indicating mechanism that can be used to tell easily whether the containment device is appropriately sized and tightened.

SUMMARY OF THE INVENTION

The present invention relates to a containment device that has an indicator or indicating mechanism that can be used to tell easily whether the containment device is appropriately sized and tightened. In one embodiment, the containment device includes a graphic indicator that can include indicium or indicia associated with the fit of the containment device. In another embodiment, the containment device includes a mechanical or stretch indicator that can change its shape or configuration based on the tightness and fit of the containment device. In another embodiment, the containment device can include a graphic indicator and a mechanical or stretch indicator.

BRIEF DESCRIPTION OF THE DRAWINGS

FIG. 11 illustrates the interaction between the closure mechanism and the indicator illustrated in FIG. 9 in another position according to the present invention.

FIG. 12 illustrates a front view of a portion of a closure mechanism in a first configuration according to the present invention.

FIG. 13 illustrates a front view of the portion of a closure mechanism illustrated in FIG. 12 in another configuration according to the present invention.

FIG. 14 illustrates a front view of the portion of a closure mechanism illustrated in FIG. 12 in another configuration according to the present invention.

FIG. 16 illustrates a front view of an alternative embodiment of a containment device according to the present invention.

FIG. 17 illustrates a front view of an embodiment of a closure mechanism according to the present invention.

FIG. 18 illustrates a front view of an alternative embodiment of a closure mechanism according to the present invention.

FIG. 19 illustrates a front view of an alternative embodiment of a closure mechanism according to the present invention.

Like reference numerals have been used to identify like elements throughout this disclosure.

DETAILED DESCRIPTION OF THE INVENTION

The present invention relates to a containment device that has an indicator or indicating mechanism that can be used to tell easily whether the containment device is appropriately sized and tightened. In one embodiment, the containment device includes a graphic indicator that can include indicia associated with the fit of the containment device. In another embodiment, the containment device includes a mechanical or stretch indicator that can change its shape or configuration based on the tightness and fit of the containment device. In another embodiment, the containment device can include a graphic indicator and a mechanical or stretch indicator.

The term "containment device" is used to refer to any type of structure that can be worn by or mounted to an infant, child, toddler, or elderly person to assist with the containment of bodily fluids and/or excrements. The terms "infant," "baby," "toddler," and "child" may be used interchangeably herein. In addition, the terms "indicator" and "indicating mechanism" may be used interchangeably herein.

Figure 1:
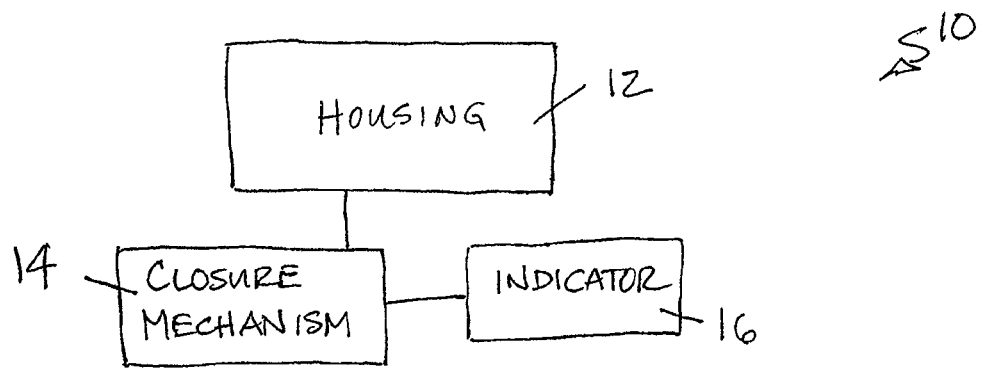
FIG. 1 illustrates a schematic block diagram of an embodiment of a containment device according to the present invention.

A schematic view of an embodiment of a containment device according to the present invention is illustrated in FIG. 1. An exemplary containment device 10 can be a diaper. In this embodiment, the containment device 10 has a housing 12 that includes a closure mechanism 14 that can be used to mount or couple the containment device 10 to a child. The containment device 10 includes an indicator 16 that is associated with the closure mechanism 14. The indicator 16 can be used by a parent or caregiver to determine whether the containment device 10 is appropriately sized as well as whether the closure mechanism 14 is too loose, too tight, or appropriately secured.

Figure 2:
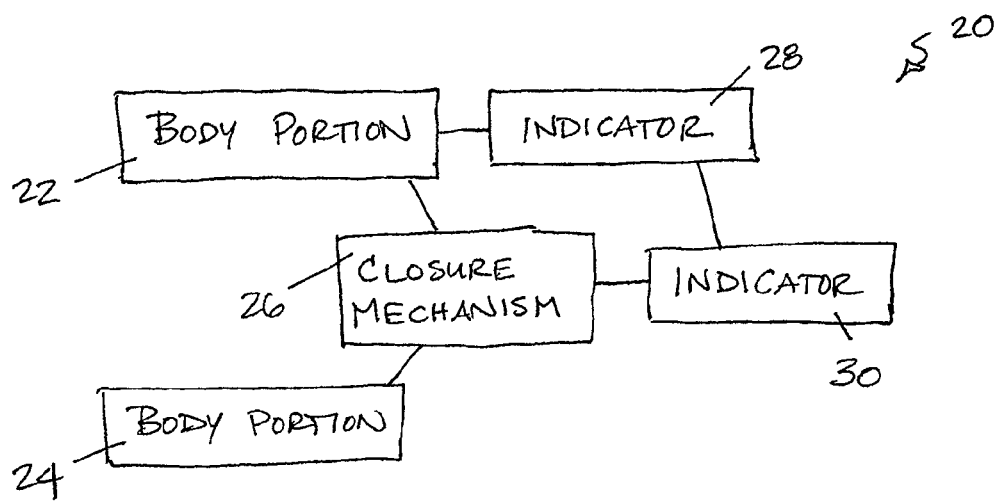
FIG. 2 illustrates a schematic block diagram of an alternative embodiment of a containment device according to the present invention.

A schematic view of an alternative embodiment of a containment device according to the present invention is illustrated in FIG. 2. In this embodiment, the containment device 20 includes two body portions 22 and 24 that can be coupled together using one or more closure mechanisms 26. In one implementation, the body portions 22 and 24 can be different parts (such as front and back parts) of a diaper. The containment device 20 may include one or more indicators 28 and 30 that can be coupled to or associated with one of the body portions 22 and 24 and closure mechanism 26. In one embodiment, the indicators 28 and 30 can be used together to determine the overall sizing and fit of the containment device 10. In another embodiment, the indicators 28 and 30 can be used separately to determine the sizing and fit of the containment device 10.

Figure 3:
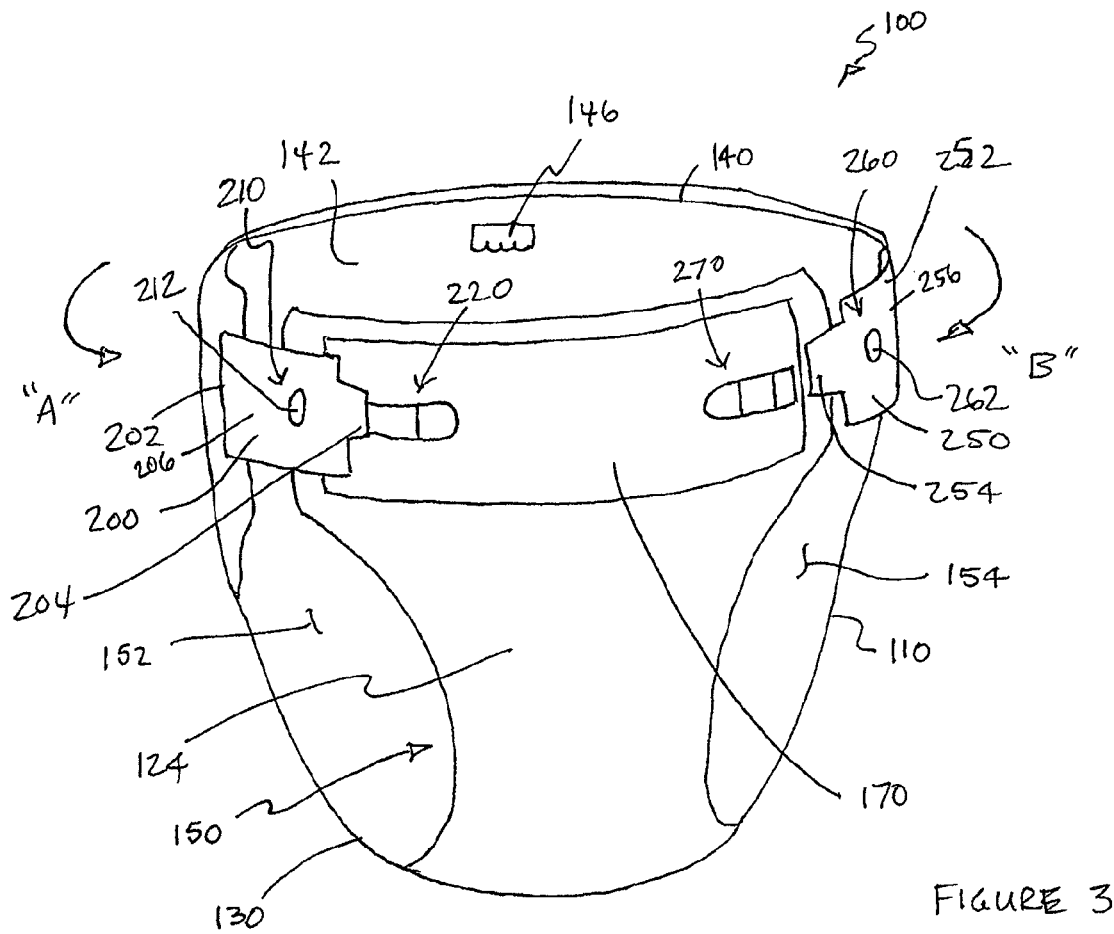
FIG. 3 illustrates a front perspective view of an alternative embodiment of a containment device according to the present invention.
Figure 4:
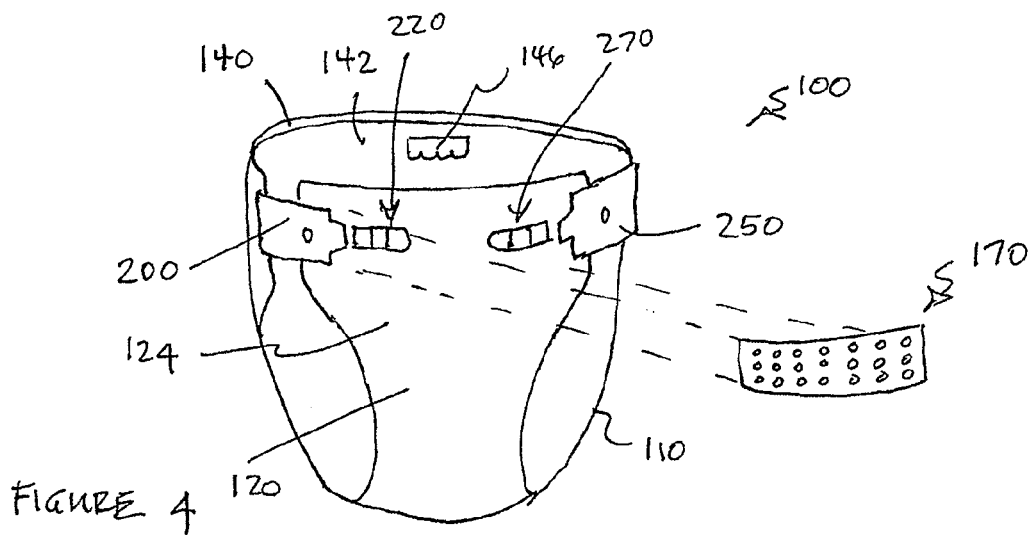
FIG. 4 illustrates an exploded front perspective view of the containment device illustrated in FIG. 3.
Figure 5:
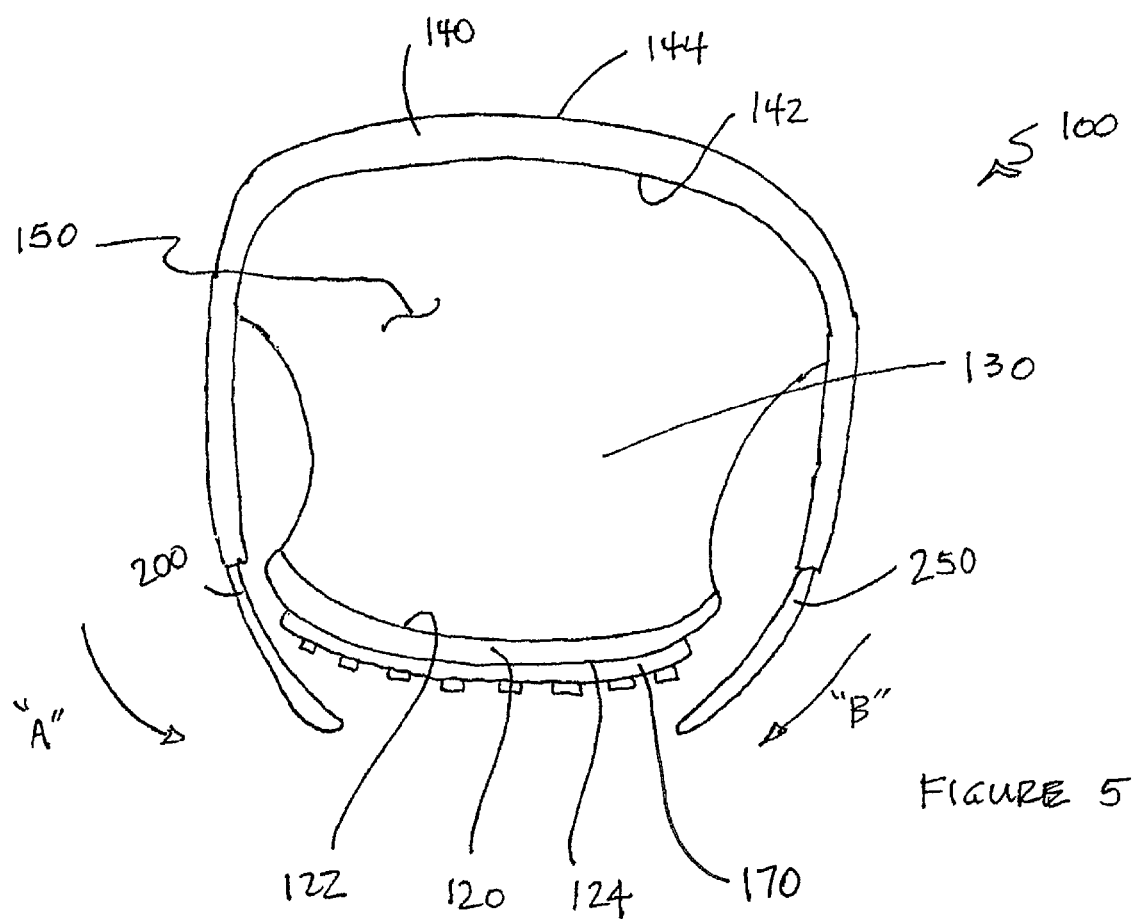
FIG. 5 illustrates a top view of the containment device illustrated in FIG. 3.

Referring to FIGS. 3-5, an embodiment of a containment device according to the present invention is illustrated. In this embodiment, the containment device 100 includes a body 110 with a front portion 120, a middle portion 130, and a rear portion 140 that collectively define a receptacle 150. The front portion 120 includes an inner surface 122 and an outer surface 124. Similarly, the rear portion 140 includes an inner surface 142 and an outer surface 144. In one embodiment, indicium 146 can be coupled to the inner surface 142 of the rear portion 140 of the containment device 100 to assist with the determination of the proper orientation of the containment device 100. For example, the indicium 146 can be used to indicate the back of the device 100. When the front portion 120 and the rear portion 140 are coupled together, openings 152 and 154 are formed through which the legs of the wearer of the containment device 100 can pass.

In one embodiment, the body 110 of the containment device or diaper chassis 100 has a printed registered poly mask/back sheet on the exterior portion of the device 100. The poly mask can be decorated using a registered location print. The location print may include graphic art, character art, machine registration markings that can be scanned for quality control during production. In one implementation, the location print can also include indicators or indicator assemblies 220 and 270 as described below. The indicators 220 and 270 are referred to as graphic indicators and can be used to assist in determining the fit, comfort and sizing for the child.

The containment device 100 includes closure mechanisms 200 and 250, such as wraps or tabs, that are used to couple the rear portion 140 to the front portion 120 to secure the containment device 100 to a child. Closure mechanism 200 includes a body 206 with ends 202 and 204. End 202 is coupled to the rear portion 140 and end 204 is a free end that is configured to be coupled to the front portion 120. Similarly, closure mechanism 250 includes a body 256 with ends 252 and 254. End 252 is coupled to the rear portion 140 and end 254 is a free end that is configured to be coupled to the front portion 120. The closure mechanisms 200 and 250 can be moved along the direction of arrows "A" and "B," respectively.

Figure 6:
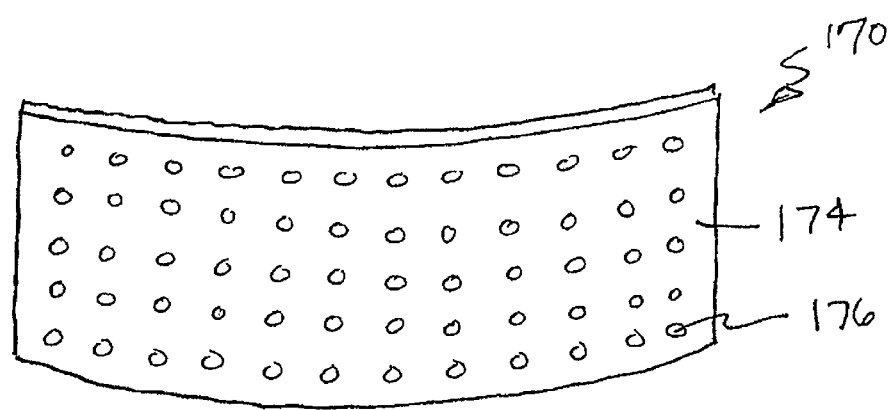
FIG. 6 illustrates a perspective view of an embodiment of a closure mechanism according to the present invention.
Figure 7:
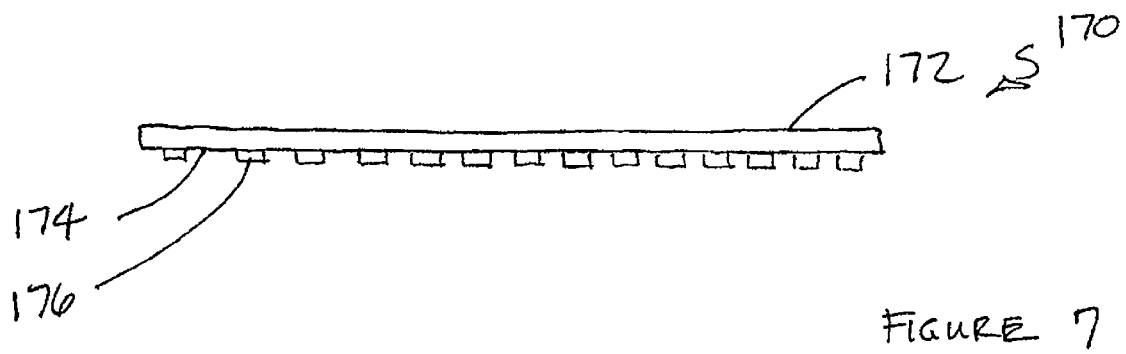
FIG. 7 illustrates a top view of the closure mechanism illustrated in FIG. 6.

In one embodiment, the containment device 100 includes a closure mechanism 170 that can be used with closure mechanisms 200 and 250 to secure the free ends 204 and 254 to the body 110. In one embodiment, closure mechanism 170 can be a tape-like structure with loop material 176 disposed around the structure. The closure mechanism 170 can be clear, transparent, or translucent and can be applied to the top of the poly mask. The closure mechanism 170 allows any printing or indicia (such as indicators 220 and 270) on the body 110 to be visible. As shown in FIGS. 6 and 7, the closure mechanism 170 includes an inner surface 172 and an outer surface 174. Several areas of loop material 176 can be disposed around the closure mechanism 170.

Each of the closure mechanisms 200 and 250 can include a hook-type material on its inner surface that is configured to engage and couple with the loop-type material 176 on closure mechanism 170. In other embodiments, the hook and loop materials can be replaced by other coupling mechanisms, such as snaps, buttons, magnets, etc.

As shown in FIGS. 3 and 4, the containment device 100 includes graphic indicators 220 and 270 which can be indicium or indicia printed on a surface of the body 110 of the device 100. The indicators 220 and 270 can be referred to as "fit zone indicators." The indicators 220 and 270 can be in the form of a graphic indicator bar or blended into the decorative graphics, such as a character or scene, that is applied to the poly mask. The graphic indicators 220 and 270 can be aligned with the closure mechanisms 200 and 250, which can also be referred to as wraps or tabs. In addition, the graphic indicators 220 and 270 can be aligned with stretch indicators 210 and 260 on closure mechanisms 200 and 250, respectively, which are described below. The indicators 210, 220, 260, and 270 can be used by a parent or caregiver to determine whether the containment device 100 has the correct size, fit or comfort for the baby or child.

The closure mechanisms 200 and 250 can be either a stretch based material or a material of limited or no elasticity. This material choice is determined by the functional expectations or requirements of the stretch indicator. The stretch indicator can vary depending on the material of the closure mechanisms. As set forth below, the stretch indicator can be either printed or die cut in the closure mechanisms. Alternatively, the stretch indicator can be overlaid with the graphic indicators.

Referring to FIGS. 3 and 4, the closure mechanisms 200 and 250 include stretch indicators or indicator assemblies 210 and 260, respectively. In one embodiment, the stretch indicators 210 and 260 are openings 212 and 262 that are formed in the closure mechanisms 200 and 250. The openings 212 and 262 can be full circles as illustrated or in other embodiments, can be partial circles or other configurations including one or more openings. In other embodiments, the stretch or mechanical indicators 210 and 260 can be printed on the closure mechanisms 200 and 250. In one example, a portion or all of the closure mechanisms 200 and 250 can be clear. One or more lines or other indicia can be provided on the closure mechanisms 200 and 250 that can change shape or configuration when the parent or caregiver pulls on the ends 204 and 254 of the closure mechanisms 200 and 250. In another embodiment, the closure mechanisms 200 and 250 are not translucent and the stretch or mechanical indicators 210 and 260 are printed thereon.

In various embodiments, the stretch indicators 210 and 260 can be arranged in a variety of ways depending on the selection of the material for the closure mechanisms 200 and 250. The closure mechanisms 200 and 250 can be either a stretch based material or a material of limited or no elasticity. The particular material used can be determined by the functional expectations or requirements of the mechanical or stretch indicators. As mentioned above, the mechanical stretch indicators 210 and 260 can be either printed or die cut in the closure mechanisms 200 and 250. If the indicators 210 and 260 include openings or translucent material, then the parent or caregiver can view indicia, such as graphic indicators 220 and 270, that is disposed beneath and overlaid by the closure mechanisms 200 and 250 when the closure mechanisms 200 and 250 are coupled to the front portion 140 of the body 110.

Figure 8:
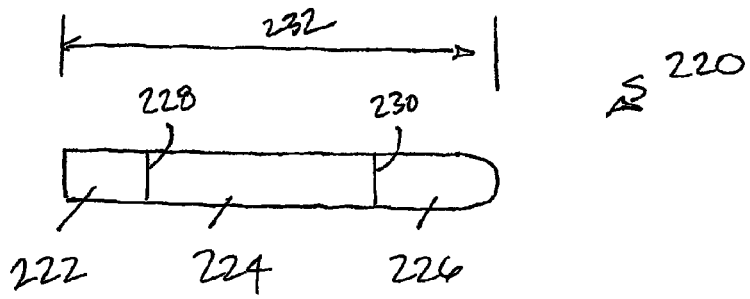
FIG. 8 illustrates a front view of an embodiment of an indicator according to the present invention.
Figure 15:
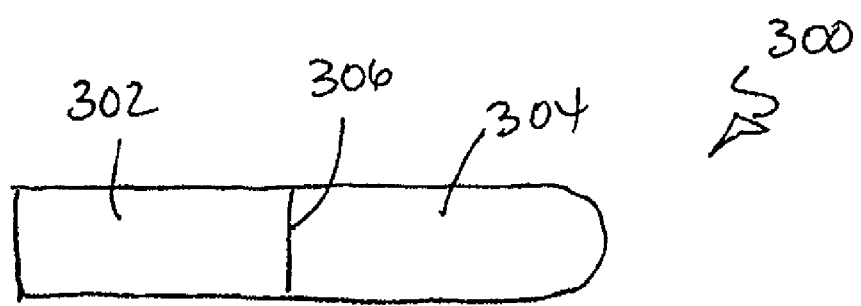
FIG. 15 illustrates a front view of an alternative embodiment of an indicator according to the present invention.

An exemplary embodiment of a graphic indicator is illustrated in FIG. 8. In this embodiment, the indicator 220 includes different indicator portions 222, 224, and 226 that are separated by lines or boundaries 228 and 230. The portions 222, 224, and 226 can be of different colors, such as red, green, and yellow, or other colors, or can be of different patterns, such as dots, stripes, circles, etc. In one embodiment, portion 222 can be red, portion 224 can be green, and portion 226 can be yellow. As described below, in one embodiment, portion 222 corresponds to the closure mechanisms 200 and 250 being too loose and/or the device 100 being too small, portion 226 corresponds to the closure mechanisms 200 and 250 being too tight and/or the device 100 being too large, and portion 224 corresponds to the closure mechanism being in a comfortable or acceptable range. The length 232 of the indicator 220, which in this embodiment is a bar or elongate member, can be selected based on the expected positions of the closure mechanisms 200 and 250 on the body 110. In other embodiments, the shape of the indicator 220 can vary as well as the quantity of portions. For example, referring to FIG. 15, indicator 300 includes two portions 302 and 304 that are separated by boundary 306.

Figure 9:
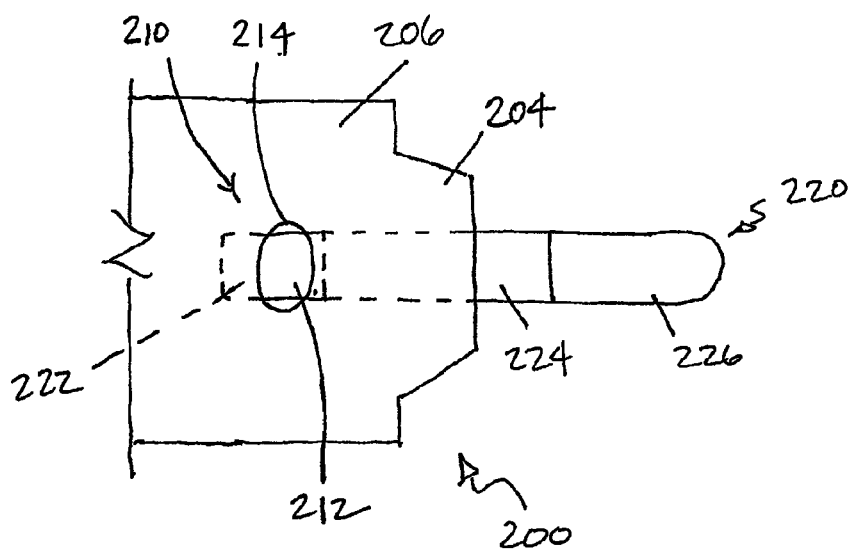
FIG. 9 illustrates the interaction between a closure mechanism and an indicator in a first position according to the present invention.
Figure 10:
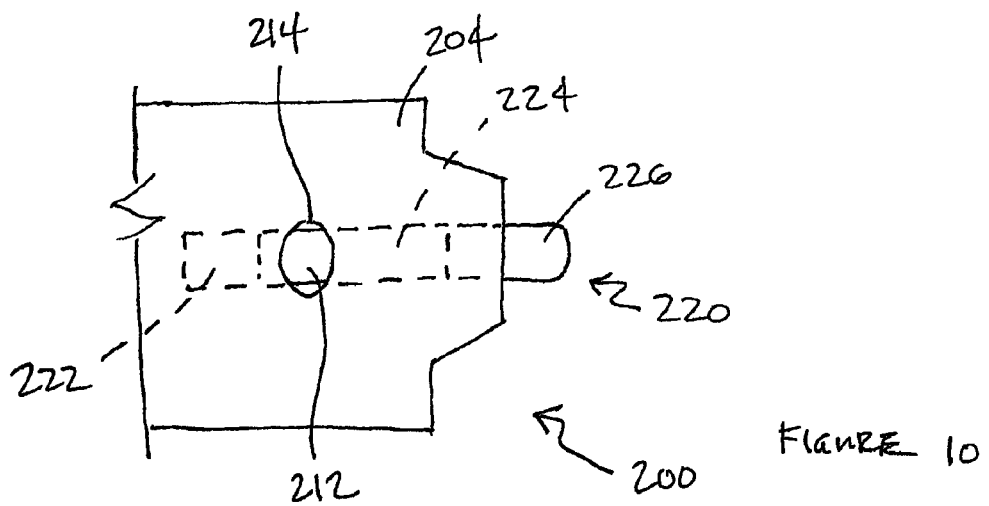
FIG. 10 illustrates the interaction between the closure mechanism and the indicator illustrated in FIG. 9 in another position according to the present invention.

Referring to FIGS. 9-11, an exemplary use of the containment device 100 according to the present invention is illustrated. While only closure mechanism 200 is described relative to FIGS. 9-11, closure mechanism 250 has the same function and features. Each of the FIGS. 9-11 illustrates the closure mechanism 200 disposed in a different position relative to the indicator 220. In one embodiment, mechanical or stretch indicator 210 can include an indicator portion 212, which is an opening defined by edge or perimeter 214. In another embodiment, mechanical or stretch indicator 210 can include an indictor portion 212, which can include a line printed on the closure mechanism instead of an opening formed therein.

Referring to FIG. 9, the end 204 of the closure mechanism 200 is positioned so that portion 222 of the graphic indicator 220 is associated with the indicator portion 212. When portion 222 is associated with, or viewable through, portion 212, the diaper chassis or containment device 100 may be too small for the child and the next size larger may be more appropriate. In addition, the closure mechanism 200 may be too loose and may need to be tightened.

Referring to FIG. 10, the end 204 of the closure mechanism 200 is located so that portion 224 of the graphic indicator 220 is associated with or viewable through the indicator portion 212. In this arrangement, the closure mechanism 200 is in an acceptable fit range and does not need to be adjusted. In addition, the size of the device 100 is likely appropriate.

Referring to FIG. 11, the end 204 of the closure mechanism 200 is positioned so that portion 226 of the graphic indicator 220 is associated with or viewable through the indicator portion 212. In this position, the diaper chassis or containment device 100 may be too large for the child and the next size smaller may be more appropriate. In addition, the closure mechanism 200 may be too tight and may need to be loosened.

In the fit determining description above, the graphic indicator 220 is used with the closure mechanism 200 and the particular shape or configuration of any indicia or any opening in the closure mechanism 200 can vary. The indicator portion 212 can be an opening, such as a slot or circle, defined by an edge or perimeter 214. In an alternative embodiment, a portion of the closure mechanism 200 can be made of a clear or translucent material and the graphic indicator 220 can be viewed therethrough. In that embodiment, a line can be provided, such as by printing, corresponding to perimeter 214, thereby simulating a shape such as a circle or opening without requiring an opening to be formed in the closure mechanism 200. Alternatively, the line can be a straight line that assists the parent or caregiver with the proper location of the closure mechanism along the graphic indicator 220 and thereby, a comfortable fit of the device 100.

While FIGS. 9-11 illustrate the use of graphic indicator 220, FIGS. 12-14 illustrate an exemplary use of a mechanical or stretch indicator according to the present invention which can be used to determine comfort, fit and proper sizing of a containment device. If the material selection for the closure mechanism 200 and 250 has some degree of elasticity, the mechanical or stretch indicator can perform in a variety of ways. In one embodiment, the mechanical or stretch indicator, which is either printed or die cut, can change shape based on the tension or force applied to the closure mechanism 200.

Referring to FIGS. 12-14, the end 204 of closure mechanism 200 is illustrated with an indicator portion having a shape such as a vertical oval 212 that is formed by an edge or perimeter 214. While only closure mechanism 200 is described relative to FIGS. 12-14, closure mechanism 250 has the same function and features. Closure mechanism 200 has a mechanical indicator 210 and also has elastic properties that enable the closure mechanism 200 to stretch, thereby changing the shape or configuration of the mechanical indicator 210.

Referring to FIG. 12, the initially vertical oval 212 has a generally circular shape or configuration 215 as defined by perimeter 214. In this case, configuration 215 indicates that the closure mechanism 200 has received a specified amount of tension so that the shape of the vertical oval is deformed into a round circle. This configuration 215 represents a comfortable fit and tightness of the containment device 100 on the child.

Referring to FIG. 13, the closure mechanism 200 has been pulled or stretched along the direction of arrow "C" more than it was in FIG. 12. As a result, the initially vertical oval 212 has a shape or configuration 216 of a horizontally oriented oval, thereby reflecting too much tension in the closure mechanism 200. Configuration 216 indicates that the closure mechanism 200 is too tight on the body of the child and needs to be loosened. In addition, the containment device 100 may be too small.

Referring to FIG. 14, the shape or configuration 218 of the initially vertical oval 212 is still a vertically oriented oval. In this case, the closure mechanism 200 has not been pulled sufficiently along the direction of arrow "D" and does not have enough tension to deform the shape of the oval 212 to a circle. Configuration 218 indicates that the closure mechanism 200 is too loose and/or too big for the body of the child and needs to be either tightened and/or replaced with a smaller containment device 100.

If the material selection for the closure mechanisms 200 and 250 has a limited or no degree of elasticity, the stretch indicator 210 can be used to define proper sizing for the child. In one implementation, the stretch indicator 210 can be either printed or die cut and has a fixed shape which does not vary when applied to the closure mechanism 200. If the stretch indicator 210 defined on one of the closure mechanisms 200 and 250 is a round or circular shape and if the particular closure mechanism 200 or 250 does not stretch when placed over graphic indicator 220 on the body 110, the parent or caregiver can examine if the size of the containment device 100 is proper for the child. For example, if the stretch indicator 210 is over portion 222 of graphic indicator 220, then the body 110 is likely too small for the child and the next size larger would be more appropriate. If the stretch indicator 210 is over portion 224 of the graphic indicator 220, then the body 110 is appropriate for the child. If the stretch indicator 210 is over portion 226 of the graphic indicator 220, then the body 110 is not appropriate for the child and the next size smaller would be more appropriate.

When a stretch indicator is used in combination with the graphic indicator, not only comfort and fit is visible to the parent or caregiver, but also proper sizing can be determined for the child.

Referring to FIG. 16, a portion of an alternative embodiment of a containment device is illustrated. The containment device 400 includes a body or front portion 410. The body 410 includes graphical indicators or indicia 420 and 430. Indicator or indicia 420 includes several portions 422, 424, and 426, which in this embodiment, are spaced apart from each other. Similarly, indicator or indicia 430 includes several spaced apart portions 432, 434, and 436. The distance between adjacent portions 422, 424, and 426 or portions 432, 434, and 436 can vary in different embodiments. In addition, the heights of the portions of indicators 420 and 430 can vary.

Referring to FIG. 17, a portion of an embodiment of a closure mechanism is illustrated. The closure mechanism 450 includes a body 452 with a distal end portion 455 that terminates in an end or edge 454. A notch 458 is formed by walls 456 that are proximate to the edge 454. The notch 458 can be referred to alternatively as a recess or an opening. The size, including the depth, and the shape of the notch 458 can vary in different embodiments. The notch 458 can be used by a parent or caregiver to view which of the portions 422, 424, and 426 is aligned with the closure mechanism 450, as described in greater detail below.

Referring to FIG. 18, a portion of an alternative embodiment of a closure mechanism is illustrated. In this embodiment, the closure mechanism 470 is generally similar to closure mechanism 450 in FIG. 17. The closure mechanism 470 includes a body 472 with a distal end portion 475 that terminates in an end or edge 474. The distal end portion 475 includes multiple notches 477 and 478 that are formed by respective edges 476. In another embodiment, a closure mechanism may include more than two notches.

Referring to FIG. 19, a portion of an alternative embodiment of a closure mechanism is illustrated. The closure mechanism 460 includes a body 462 with a distal end portion 465 that terminates in an end or edge 464. The edge 464 includes several recesses 466 spaced apart therealong. There are openings 468 formed in the distal end portion 465 that extend therethrough. The openings 468 can be sized so that a parent or caregiver can see through the openings 468 to the front surface of the body 410 of the containment device 400 below the closure mechanism 460. Accordingly, the caregiver can determine the relative position of the closure mechanism 460 and whether the fit of the containment device 400 is acceptable. For example, if the portions 422, 424, and 426 are different colors, the caregiver can see which color is aligned with and visible through the openings 468. The quantity and sizes of the openings 468 can vary in different embodiments.

Figure 20:
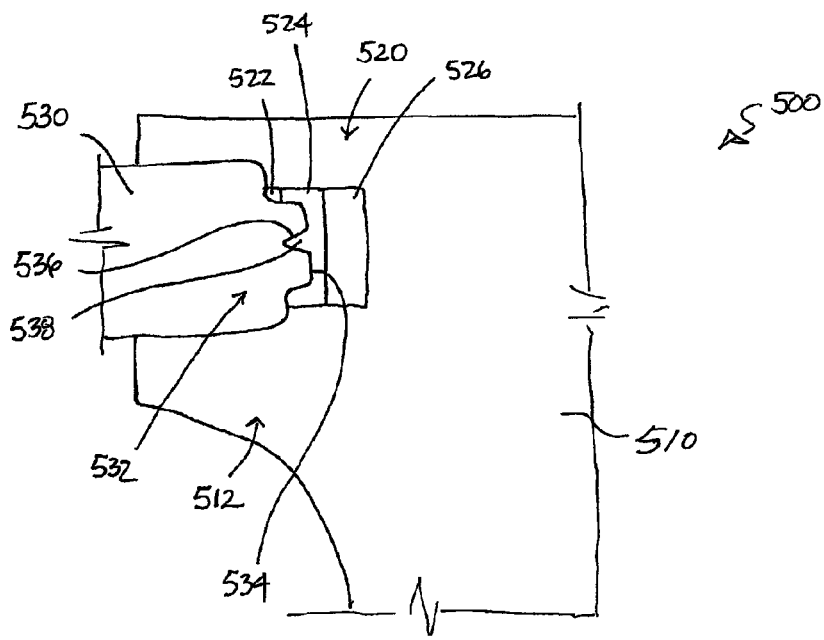
FIG. 20 illustrates a front view of a closure mechanism coupled to a portion of a containment device according to the present invention.

Referring to FIG. 20, a closure mechanism is illustrated as being coupled to a portion of a containment device. In this embodiment, the containment device 500 includes a body 510, of which only a portion is shown for ease of reference. The body 510 includes a side portion 512 that includes an indicator or indicia 520. In various embodiments, the indicia 520 can vary in size and in quantity. In this embodiment, the indicia 520 includes portions 522, 524, and 526 which can be different colors, such as yellow, green, and red, to indicate different fits of the containment device 500.

As shown in FIG. 20, a closure mechanism 530 can be used with the indicia 520 on the body 510. Closure mechanism 530 includes a body with a distal end portion 532 and an end or edge 534. An edge 536 is formed in the distal end portion 532 and defines a notch or opening 538. The notch 538 can be used by a parent or caregiver to determine the particular portion 522, 524, or 526 with which the distal end portion 532 is aligned. In FIG. 20, the notch 538 is aligned with portion 524, which can be representative of a desired fit of the containment device 500.

Figure 21:
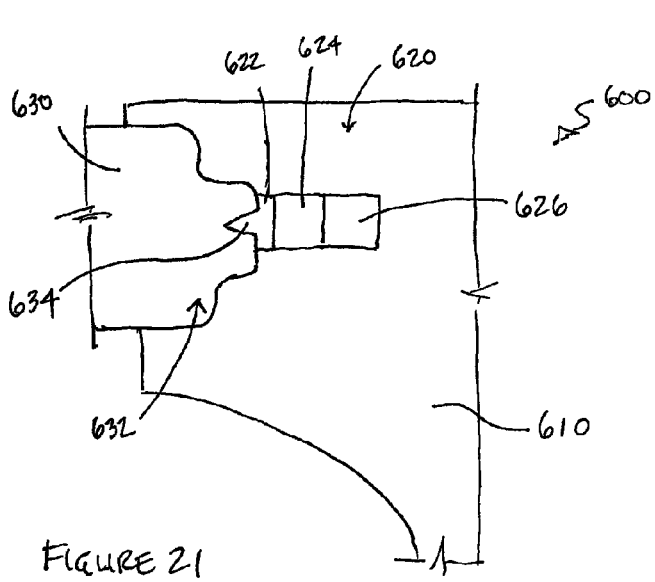
FIG. 21 illustrates a front view of a closure mechanism coupled to a portion of a containment device according to the present invention.
Figure 22:
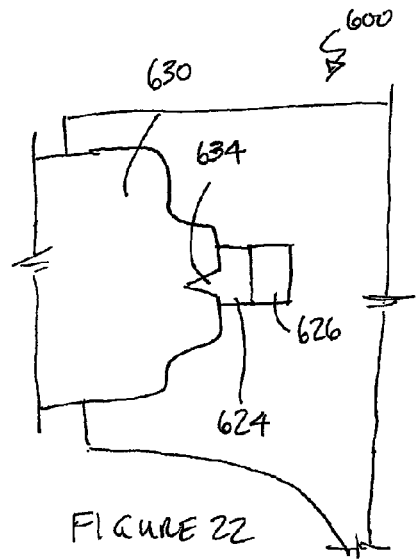
FIG. 22 illustrates a front view of the closure mechanism and the containment device illustrated in FIG. 21 coupled together in a second position.

Referring to FIGS. 21 and 22, an alternative embodiment of a containment device is illustrated. In this embodiment, the height of the portions 622, 624, and 626 of the indicia 620 on body 610 of containment device 600 is less than the height of the distal end portion 632 of the closure mechanism 630. Accordingly, the notch 634 that is formed in the distal end portion 632 is needed to determine the particular portion 622, 624, or 626 with which the closure mechanism 630 is aligned. In FIG. 21, the end of the closure mechanism 630 is aligned with portion 622. Referring to FIG. 22, the closure mechanism 630 is illustrated in a different position in which the notch 634 is aligned with portion 624.

Figure 23:
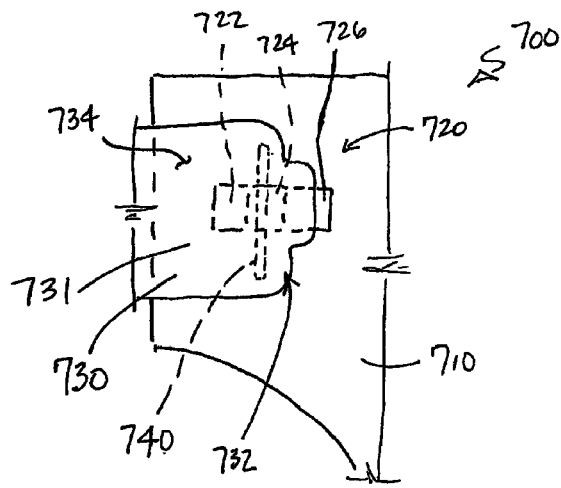
FIG. 23 illustrates a front view of an alternative embodiment of a closure mechanism coupled to a containment device according to the present invention.
Figure 24:
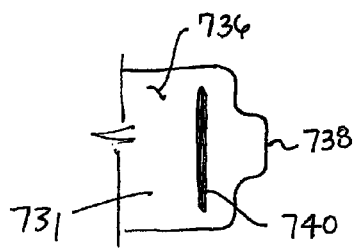
FIG. 24 illustrates a rear view of the closure mechanism illustrated in FIG. 23.

Referring to FIGS. 23 and 24, an alternative embodiment of a portion of a containment device according to the present invention is illustrated. The containment device 700 includes a body 710 with an indicator or indicia 720 with portions 722, 724, and 726. In this embodiment, the closure mechanism 730 has a body 731 that is transparent or semi-transparent so that a caregiver can see therethrough. As shown in FIG. 23, the portions 722, 724, and 726 are illustrated in dashed lines, which indicates that the portions 722, 724, and 726 can be viewed through the body 731.

The body 731 includes a distal end portion 732 and an outer surface 734 as shown in FIG. 23. Referring to FIG. 24, the body 731 also includes an inner surface 736 that is opposite to surface 734 (shown in FIG. 23). The closure mechanism 730 also includes indicia 740 that can be used to determine the alignment of the closure mechanism 730 on the body 710 of the containment device 700. In one embodiment, the indicia 740 can be an elongate mark or line that can be placed and marked onto the inner surface 736 of the body 731 (see FIG.

24). Alternatively, the indicia 740 can be on the outer surface of body 731. The indicia 740 can be spaced apart from end 738.

In one implementation, the closure mechanism 730 may be extruded and the indicator 740 formed in the closure mechanism 730 during the extruding process. In another implementation, the indicia 740 can be formed as part of the closure mechanism 730. In another implementation, the closure mechanism 730 may include a tape-like portion that have a hook or loop-type material. The tape can be extruded to be formed and the desired color or marking can be injected into the tape material before it is extruded. The tape that is applied to the top of the poly mask can be translucent so that it allows the graphic indicator to remain visible. In alternative embodiments, the tape does not include any additional printings or markings.

Figure 27:
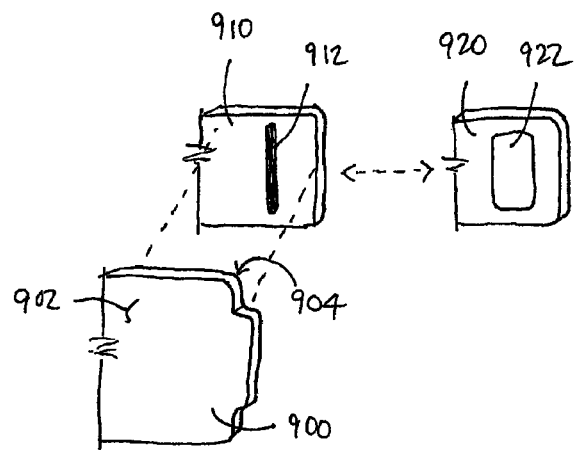
FIG. 27 illustrates an exploded perspective view of alternative embodiments of couplers for a closure mechanism according to the present invention.

Referring to FIG. 27, the closure mechanism 900 includes a body 902 with an inner surface 904 to which a tape portion 910 with an indicator or indicia 912 can be coupled using any conventional technique, such as an adhesive. If the body 902 of the closure mechanism 900 is transparent or semi-transparent, the indicator 912 will be viewable through the body 902.

Figure 25:
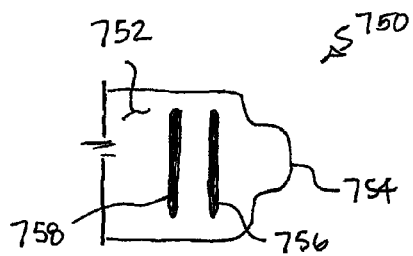
FIG. 25 illustrates a rear view of an alternative embodiment of a closure mechanism according to the present invention.

Referring back to FIG. 25, an alternative embodiment of a closure mechanism is illustrated. In this embodiment, the closure mechanism 750 includes a body 752 with a distal end portion 754 and multiple indicators or indicia 756 and 758. In different embodiments, the sizes and configurations of the indicators 756 and 758 can vary.

As shown in FIG. 23, the indicia 740 on the closure mechanism 730 can be used to determine the alignment of the closure mechanism 730 with the body 710 of the containment device 700. In particular, the indicia 740 is aligned with one of the portions 722, 724, or 726 when the closure mechanism 730 is coupled to the body 710. In the illustrated example, the indicia 740 is aligned with portion 724, which in one implementation, can correspond to the desired fit of the containment device 700 on the individual. For closure mechanism 750 (see FIG. 25), the indicators 756 and 758 are utilized together to allow a parent or caregiver to confirm the fit of the containment device 700. In other words, the appropriate fit of the containment device 700 may be coordinated such that portion 724 is to be between lines 756 and 758.

In an alternative embodiment in which the closure mechanism 730 is opaque, the indicia 740 can still be used to determine the particular fit of the containment device 700. When the caregiver is placing the containment device 700 on an individual, the caregiver can place the closure mechanism 730 proximate to the target or landing zone on the body 710 (where indicia 720 is located). As the closure mechanism 730 moves closer to the body 710, the caregiver can see with which of the portions 722, 724, and 726 the indicator 740 is aligned.

Figure 26:
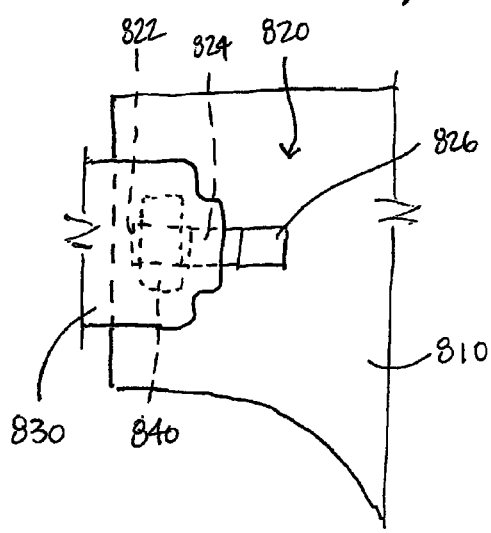
FIG. 26 illustrates a front view of an alternative embodiment of a closure mechanism coupled to a containment device according to the present invention.

Referring to FIG. 26, an alternative embodiment of a containment device according to the present invention is illustrated. In this embodiment, the containment device 800 includes a body 810 with an indicator or indicia 820 with several portions 822, 824, and 826. Instead of being a single elongate line, indicator 840 on the closure mechanism 830 can be an area or region, which in one embodiment, has a particular color. For example, indicator 840 can be an area that is the color green. Accordingly, a caregiver is to match up the indicator 840 with the desired portion of the indicator 820, which in one implementation, can be portion 824 which can be green as well.

The body of the closure mechanism 830 can be transparent or semi-transparent, thereby permitting a caregiver to view the indicator 840 and the portions 822, 824, and 826 therethrough. Each of the portions 822, 824, and 826 can be a different color, thereby facilitating the distinction between the portions 822, 824, and 826. The containment device 800 has a proper fit when the indicator 840 is aligned with the corresponding portion 822, 824, or 826 of indicator 820 as desired. In another embodiment, the body of the closure mechanism 830 can be opaque. The caregiver can move the closure mechanism 830 close to the indicators 820 and see with which of the portions 822, 824, and 826 the indicator 840 is aligned.

Referring to FIG. 27, an exemplary portion of hook or loop-type material tape or other coupler 920 can be coupled to the inner surface 904 of the closure mechanism 900. The coupler 920 may include an indicator 922 formed on or within the coupler 920. In one embodiment, the coupler 920 may be used alternatively to portion 910.

In different embodiments, the locations, sizes, configurations, patterns, colors and other features of the indicators or indicia can vary.

While the invention has been described in detail and with reference to specific embodiments thereof, it will be apparent to one skilled in the art that various changes and modifications can be made therein without departing from the spirit and scope thereof. For example, it is to be understood that terms such as "first," "second," "top," "bottom," "front," "rear," "side," "height," "length," "width," "upper," "lower," "interior," "exterior," "inner," "outer," and the like as may be used herein, merely describe points of reference or different elements and do not limit the present invention to any particular orientation or configuration. Thus, it is intended that the present invention covers the modifications and variations of this invention provided they come within the scope of the appended claims and their equivalents.

What is claimed is:

1. A containment device comprising:
a body having a first portion and a second portion;
a closure mechanism being coupled to the first portion and selectively coupleable to the second portion to couple the first portion to the second portion;
a first indicator located on the second portion, the closure mechanism being positionable proximate to the first indicator, the first indicator being used to indicate the appropriateness of the size of the containment device; and
a second indicator located on the closure mechanism, the second indicator being used to indicate the tension applied to the closure mechanism.

2. The containment device of claim 1, wherein the first indicator is a graphic indicator having at least two different portions.

3. The containment device of claim 2, wherein each of the portions of the first indicator has one of a color and a pattern different than the other portions of the first indicator.

4. The containment device of claim 1, wherein the first indicator includes a first indicator portion associated with the body being too small for an individual, a second indicator portion associated with the body being properly sized for the individual, and a third indicator portion associated with the body being too large for the individual.

5. The containment device of claim 1, wherein the closure mechanism includes a body with a distal end portion that has an edge, the edge including at least one recess formed therein, the recess being alignable with the first indicator so that the portion of the first indicator with which the closure mechanism is aligned can be viewed.

6. The containment device of claim 5, wherein the distal end portion includes at least one opening formed therein, the opening being sized to permit a user to see therethrough.

7. The containment device of claim 1, wherein the second indicator is an opening formed through the closure mechanism.

8. The containment device of claim 7, wherein the shape of the opening changes when the tension applied to the closure mechanism changes.

9. The containment device of claim 1, wherein the closure mechanism is translucent and the second indicator is a line formed on the closure mechanism, the line being viewable through the closure mechanism.

10. The containment device of claim 1, wherein the second indicator is an opening formed in the closure mechanism, the closure mechanism being coupleable to the second portion such that the first indicator is visible through the second indicator.

11. A diaper comprising:
a body having a front portion, a middle portion, and a rear portion, each of the front portion and the rear portion including a closure mechanism coupled thereto, the closure mechanism of the rear portion being engageable with the closure mechanism of the front portion to couple the rear portion to the front portion;
a first indicator assembly located on the front portion, the closure mechanism of the rear portion being placeable proximate to the first indicator assembly, the first indicator assembly indicating the appropriateness of the size of the diaper; and
a second indicator assembly formed on the closure mechanism of the rear portion, the second indicator assembly indicating the tension applied to the closure mechanism of the rear portion.

12. The diaper of claim 11, wherein the second indicator assembly is placeable proximate to the first indicator assembly.

13. The diaper of claim 12, wherein the second indicator assembly includes an opening formed in the closure mechanism of the rear portion, the opening being configured so that the first indicator assembly can be viewed therethrough.

14. The diaper of claim 13, wherein the configuration of the opening varies depending on the tension applied to the closure mechanism of the rear portion.

15. The diaper of claim 11, wherein the first indicator assembly includes at least two portions, each of the portions of the first indicator assembly indicating a different size appropriateness of the body, the second indicator assembly being alignable with the portions of the first indicator assembly.

16. A diaper body comprising:
a front portion;
a rear portion;
a middle portion located between the front portion and the rear portion, the front portion, the rear portion, and the middle portion collectively defining a receptacle;
a first tab coupled to the rear portion, the first tab being engageable with the front portion to couple the rear portion to the front portion, the first tab including a first indicator configured to indicate the tension applied to the first tab when the first tab is engaged with the front portion; and
a second tab coupled to the rear portion, the second tab being engageable with the front portion to couple the rear portion to the front portion, the second tab including a second indicator configured to indicate the tension applied to the second tab when the second tab is engaged with the front portion.

17. The diaper body of claim 16, wherein the first indicator is an opening formed in the first tab and the second indicator is an opening formed in the second tab.

18. The diaper body of claim 17, wherein the opening in the first tab has a first configuration when no tension is applied to the first tab and a second configuration when tension is applied to the second tab, the first configuration being different than the second configuration.

19. The diaper body of claim 18, wherein the first configuration of the opening is an oval and the second configuration of the opening is a circle.

20. The diaper body of claim 16, wherein the first tab includes a translucent portion and the first indicator is indicium located on the first tab proximate to the translucent portion, the indicium being viewable through the first tab.

* * * * *